(12) United States Patent
Vijay et al.

(10) Patent No.: US 7,988,933 B2
(45) Date of Patent: Aug. 2, 2011

(54) IDENTIFICATION SYSTEM FOR A CLINICAL SAMPLE CONTAINER

(75) Inventors: Tumkur R. Vijay, Newark, DE (US); Randall R. Davis, Bear, DE (US); David R. Thompson, Kennett Square, PA (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 981 days.

(21) Appl. No.: 11/846,666

(22) Filed: Aug. 29, 2007

(65) Prior Publication Data

US 2008/0056958 A1 Mar. 6, 2008

Related U.S. Application Data

(60) Provisional application No. 60/824,337, filed on Sep. 1, 2006.

(51) Int. Cl.
*G01N 31/22* (2006.01)
(52) U.S. Cl. ........ 422/404; 422/400; 422/401; 422/403; 422/568; 422/119
(58) Field of Classification Search .......... 422/400–404, 422/568, 119
See application file for complete search history.

(56) References Cited

U.S. PATENT DOCUMENTS

| | | |
|---|---|---|
| 4,729,661 A | 3/1988 | Bell |
| 4,805,772 A | 2/1989 | Shaw et al. |
| 5,137,693 A | 8/1992 | Mawhirt |
| 5,186,339 A | 2/1993 | Heissler |
| 5,201,232 A * | 4/1993 | Uffenheimer ............... 73/864.23 |
| 5,456,887 A | 10/1995 | Calvo et al. |
| 5,517,867 A * | 5/1996 | Ely et al. ..................... 73/863.85 |
| 5,672,317 A | 9/1997 | Buhler et al. |
| 5,687,849 A | 11/1997 | Borenstein et al. |
| 5,700,429 A | 12/1997 | Buhler et al. |
| 5,985,215 A * | 11/1999 | Sakazume et al. ............. 422/67 |
| 6,081,326 A | 6/2000 | Rousseau et al. |
| 6,141,602 A * | 10/2000 | Igarashi et al. ............... 700/226 |
| 2002/0009395 A1* | 1/2002 | Hirono et al. .................. 422/67 |
| 2003/0161764 A1 | 8/2003 | Itoh |
| 2004/0226984 A1* | 11/2004 | Smith et al. ................... 228/101 |
| 2005/0130220 A1 | 6/2005 | Lemmo et al. |
| 2006/0000296 A1 | 1/2006 | Salter |
| 2008/0056956 A1* | 3/2008 | Vijay et al. .................... 422/103 |

FOREIGN PATENT DOCUMENTS

EP 0 295 047 A2 12/1988
EP 1 614 476 A1 1/2006

OTHER PUBLICATIONS

Fiore et al. The Abbott IMx automated benchtop immunochemistry analyzer system:. In: Clinical Chemistry [online], vol. 34, p. 1726-1732. Published Jun. 14, 1988. [retrieved on Sep. 17, 2008]. Retrieved from the Internet: <URL:http://www.clinchem.org/cgi/reprint/34/9/1726.pdf>.
European Search Report Sep. 30, 2010 Application No. 07841586.6.

* cited by examiner

*Primary Examiner* — Jyoti Nagpaul
(74) *Attorney, Agent, or Firm* — Leland K. Jordan (57) ABSTRACT

A clinical analyzer with a vision system proximate a sample tube rack, the rack having a number of different insert adapters, the adapters having markings to identify the insert, thereby identifying the type of tube. The adapters are of heights selected to position tubes of various heights at a common aspiration level. A 2-D imaging device is employed to read the markings and for analyzing various distinguishing characteristics of the sample tubes.

13 Claims, 7 Drawing Sheets

IDENTIFICATION SYSTEM FOR A CLINICAL SAMPLE CONTAINER

REFERENCE TO RELATED APPLICATIONS

This application claims benefit of U.S. Provisional Application 60/824,337 filed Sep. 1, 2006.

FIELD OF THE INVENTION

The present invention relates to a system for identifying clinical sample containers. In particular, the present invention provides an improved method for identifying a particular one of a number of different types of sample tubes containing patient samples for analysis within an automatic clinical analyzer.

BACKGROUND OF THE INVENTION

Various types of analytical tests related to patient diagnosis and therapy can be performed by analysis of a liquid sample taken from a patient's infections, bodily fluids or abscesses. These assays are typically conducted with automated clinical analyzers onto which tubes or vials containing patient samples have been loaded. The analyzer extracts liquid sample from the vial and combines the sample with various reagents in special reaction cuvettes or tubes. Usually the sample-reagent solution is incubated or otherwise processed before being analyzed. Analytical measurements are often performed using a beam of interrogating radiation interacting with the sample-reagent combination to generate turbidimetric, fluorometric, absorption readings or the like. The readings allow determination of end-point or rate values from which an amount of analyte related to the health of the patient may be determined using well-known calibration techniques.

An important contributor to maintaining a high efficiency in throughput of patient samples is the ability to quickly and securely introduce a plurality of samples into the sample testing portion of an analyzer. Patient samples are typically held in a container such as a test tube, and the test tubes placed into a sample rack adapted to support multiple sample containers generally in an upright orientation.

The sample rack is typically placed in an input portion of the analyzer, identified as to type of tube, and moved to a location where a portion of the liquid patient sample is extracted usually by aspiration using a hollow, needle like probe from the tube for testing by the analyzer. Afterwards, the sample rack may be moved to temporary storage area or to an output portion of the analyzer where the user can conveniently remove the sample rack from the analyzer.

Patient samples are known to be provided to such analyzers in a number of different types of tubes. In particular, tubes having 13 mm and 16 mm diameters are popular in a number of different heights and "small sample" tubes, sometimes called small sample cups SSC are typically used for pediatric samples. Sample tube racks have been developed to accommodate different tubes like those described and these racks generally have a vertical opening to enable a bar code reader to read a linear bar code affixed to each tube in order to identify the patient's identity. These markings are generally 1-D, rectilinear and are also provided to assist tracking a tube within the analyzer and to control the mode of aspiration (speed, depth, through-the-stopper or not, and the like). After being placed on the analyzer, a predetermined, known portion of the original sample is aspirated from the tube and analytical tests conducted thereon.

A problem with aspirating a known quantity of sample from a number of different types of tubes arises when different tube types are presented to an aspiration probe or needle. The level of liquid in different tube types varies and the volume of liquid between levels in tubes with different diameters varies. Therefore, when a sample tube is presented to an aspiration probe, in order to aspirate a predetermined, known portion of original sample, the aspiration process must take into account the upper level of liquid, the diameter of the sample tube, as well as the maximum depth available for aspiration.

One solution to this problem requires that an operator place specific size and shape sample tubes in pre-defined slots within a specific sample rack and to ensure that a marking is properly affixed to the tube and oriented in the rack so as to be readable. This requires careful operator attention and introduces a source of error.

U.S. Pat. No. 6,081,326 provides a sample tube carrier especially designed to enable reading of identification codes ascribed on the walls of sample tubes by using a rotary drive to rotate the tube during a code reading process.

U.S. Pat. No. 5,186,339 provides a sample tube rack having similar receptacles with removable base portions and with insertable adapters to accommodate sample tubes of different lengths and diameters. An aperture is formed in the exterior wall to facilitate scanning the containers. U.S. Pat. No. 5,137,693 provides similar adapters to accommodate different size tubes in a test tube holder, the holders having an axial slot for optical viewing of a tube to ascertain its presence. U.S. Pat. No. 5,687,849 also provides moveable collar members to accommodate different diameter tubes in a test tube holder having a viewing slot for observing tubes.

For obvious reasons, it would be highly desirable for an operator to have the freedom to place any tube at any location in a rack and be freed of other restrictions.

From the above descriptions of the art, it is apparent that, while progress has been made in this direction, what has been overlooked is that the small size of some tubes dictates that a "small print" linear marking for identification be used, thereby introducing a large source of error in identifying tube types.

SUMMARY OF THE INVENTION

The present invention provides an optical imaging system and a sample tube rack, the rack having a number sample tube openings in parallel rows, the opening capable of containing different insert adapters. The adapters are provided with special, high-contrast, reflective 2-D identification markings to enable accurate identification of the insert. By selectively associating different tube types with different insert adapters, the type of sample container tube can be distinguished by identification of the insert. Advantageously, the adapters are of varying heights so as to position tubes of various heights and diameters at a common aspiration level. The optical imaging system employs a 2-D imaging device to read the 2-D insert identification markings and also to identify various characteristics of the sample tube container. Identifiable tube container characteristics include tube barcode, presence or absence of a tube cap and whether the container is a SSC. In order to increase analyzer tube processing, the imaging system is configured so as to simultaneously identify two tubes on opposite sides of a sample rack having parallel rows of sample tube openings. The imaging system is further configured with angled reflective mirror surfaces so as to occupy minimal space on the analyzer.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
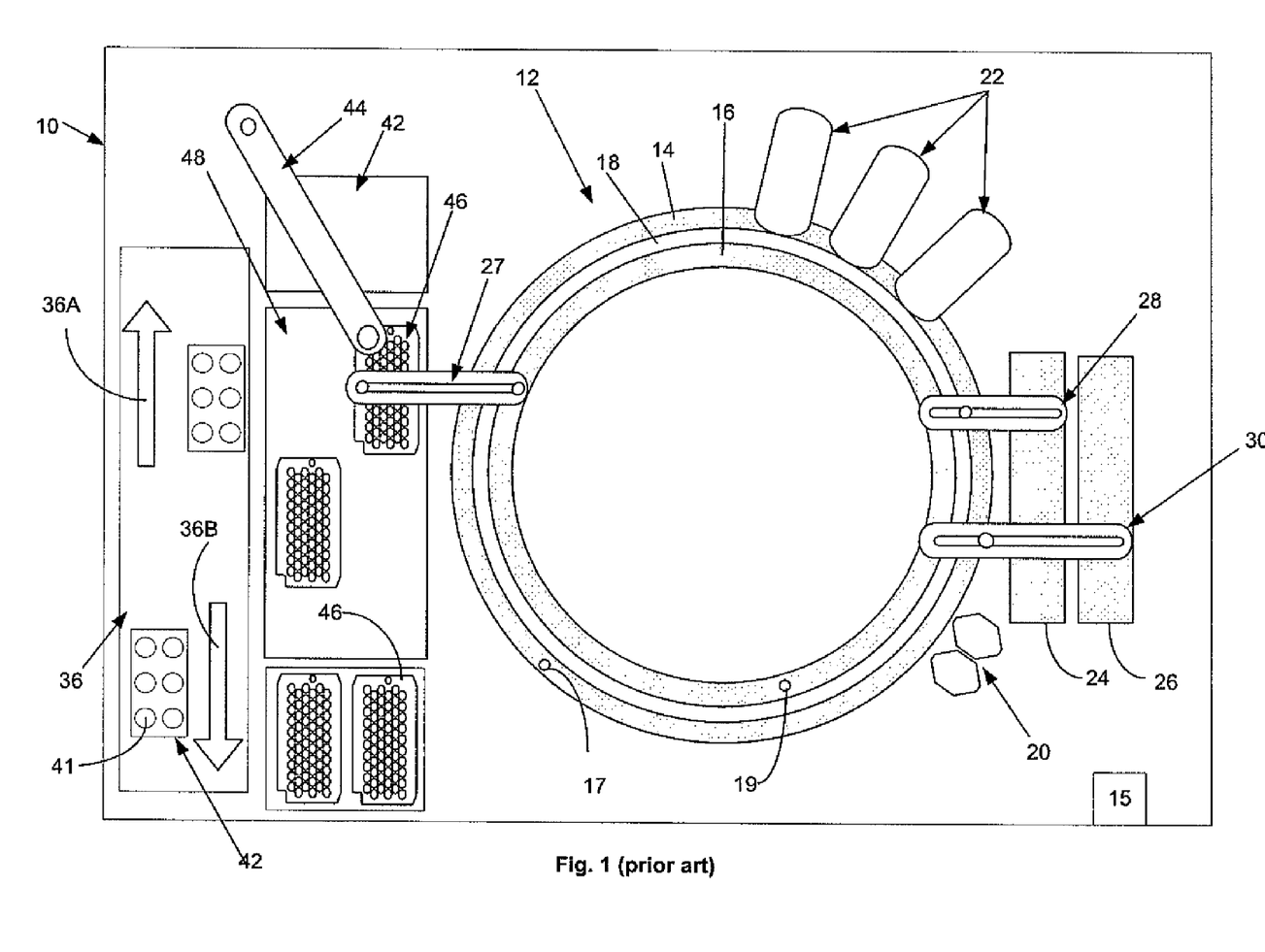
FIG. 1 is a schematic plan view of an automated clinical analyzer in which the present invention my be advantageously employed.

FIG. 1 shows schematically the elements of a conventional automatic chemical analyzer 10 in which the present invention may be advantageously practiced. Analyzer 10 comprises a reaction carousel 12 with an outer cuvette circle 14 supporting cuvettes 17 and an inner cuvette circle 16 supporting cuvettes 19, the outer cuvette circle 14 and inner cuvette circle 16 separated by a groove 18. Reaction carousel 12 is rotatable using stepwise movements in a constant direction at a constant velocity, the stepwise movements being separated by a constant dwell time during which dwell time, carousel 12 is maintained stationary and individual computer controlled electro-mechanical devices 20, such as sensors, reagent add stations, mixing stations, and the like, perform the actions required in well known clinical assays. Temperature-controlled reagent storage areas 24 and 26 store a plurality of reagent containers containing reagents placed into cuvettes 17 and 19 by probes 28 and 30 as necessary to perform a given assay. Various assay analyzing means 22 may be located proximate carousels 14 and 16 and are adapted to measure light absorbance in or emission from cuvettes 17 and 19 at various wavelengths, from which the presence of analyte in the sample liquid may be determined using known analytical techniques.

Such devices and their control and operation are described, for example, in U.S. Pat. Nos. 5,876,668, 5,575,976 and 5,482,861 and the references cited therein, all of which are incorporated by reference for enablement.

Analyzer 10 is controlled by computer 15 based on software written in a machine language, like that used on the Dimension® clinical chemistry analyzer sold by Dade Behring Inc, of Deerfield, Ill., and widely used by those skilled in the art of computer-based electromechanical control programming to perform assays and related operations given the identity of a patient sample, assay requests, and the like.

Figure 2:
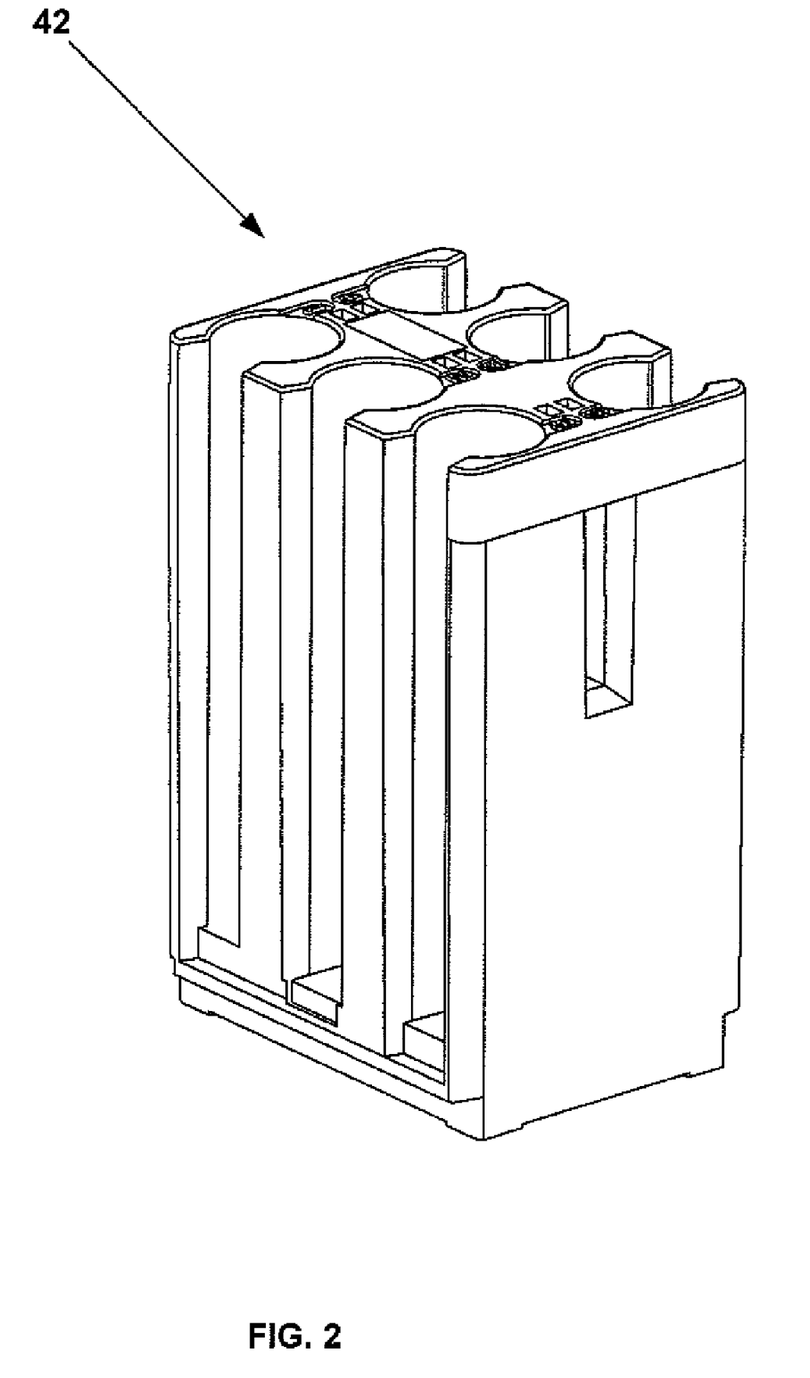
FIG. 2 is a perspective view of a sample rack exemplary for use in an automatic clinical analyzer like see in FIG. 1.

Incoming sample samples to be tested are typically contained in sample containers or tubes 40 supported in sample tube racks 42 like seen in FIG. 2 and transportable by a sample tube rack transport system 36 comprising incoming lane 36A and outgoing lane 36B. Aliquot probe 44 is conventionally controlled by computer 15 to aspirate liquid sample from sample tubes 40 and to dispense one or more aliquot portions of the original patient sample into aliquot arrays 46 carried on an aliquot transport system 48 using probe 27 depending on the quantity of sample required to perform the requisite assays and to provide for at least one aliquot portion to be retained by analyzer 10.

In present analyzers, an operator is required to place specific size & shape sample tubes 40 in pre-defined slots or openings 41 within a specific sample rack 42 and to ensure that a marking is properly affixed to tube 40 and oriented in rack 42 so as to be readable. These markings are generally 1-D, rectilinear. The purpose of these requirements is to be able to track a tube within the analyzer and to control the mode of aspiration (speed, depth, Through The Stopper or not, and the like). For obvious reasons, it would be highly desirable for an operator to have the freedom to place any tube 40 at any place in any rack 42 and be freed of other restrictions.

The present invention uses a number of different inserts with special, high-contrast, reflective 2-Dimension (2-D) markings to identify the insert and position sample tubes 40 of various heights and diameters at a common aspiration level, thereby also identifying the type of tube. A 2-D imager 54 is employed to read the 2-D marks and for analyzing various distinguishing shapes of the sample tubes. In particular, sample tubes 40 are scanned using the vision system 50 of the present invention illustrated in FIG. 3, a perspective schematic of vision system 50 showing the relative positioning of imagers 54, mirrors 52 and an opaque reflector 55 as well as the path of interrogating radiation, shown as dashed line RAD. and in the simplified top plan view of FIG. 4. Imagers 54 are like 2-D CMOS imagers 54 with 640×480 pixel resolution for identification of the various test tube 40 types that are potentially present in a rack 42 like seen in the simplified top plan schematic view of FIG. 4. Imagers like CMOS imagers 54 are available from JADEK Technologies, Kit 1090, such vision kits usually containing identification software programs executed on a remote host computer or optionally on computer 15. Image analysis software having extensive enhancement and measurement tools for providing a full range of utilities for capturing, communicating, processing, measuring, analyzing, archiving, reporting, and printing data are known and commercially available from companies such as Media Cybernetic, Bethesda, Md. and Sharpimage Software, Brooklyn, N.Y. Reflector 55 is shown as located between the two rows on sample tubes 40 held in rack tube openings or slots in rack 42, reflector 55 being opaque and comprising opposed retro-reflective surfaces that provide a consistent background for tube shape image processing. Retro-reflective surfaces contain crushed glass beads and are covered with a protective laminate and are commercially available from companies like ID Label, Inc., Lake Villa, Ill.

Figure 5:
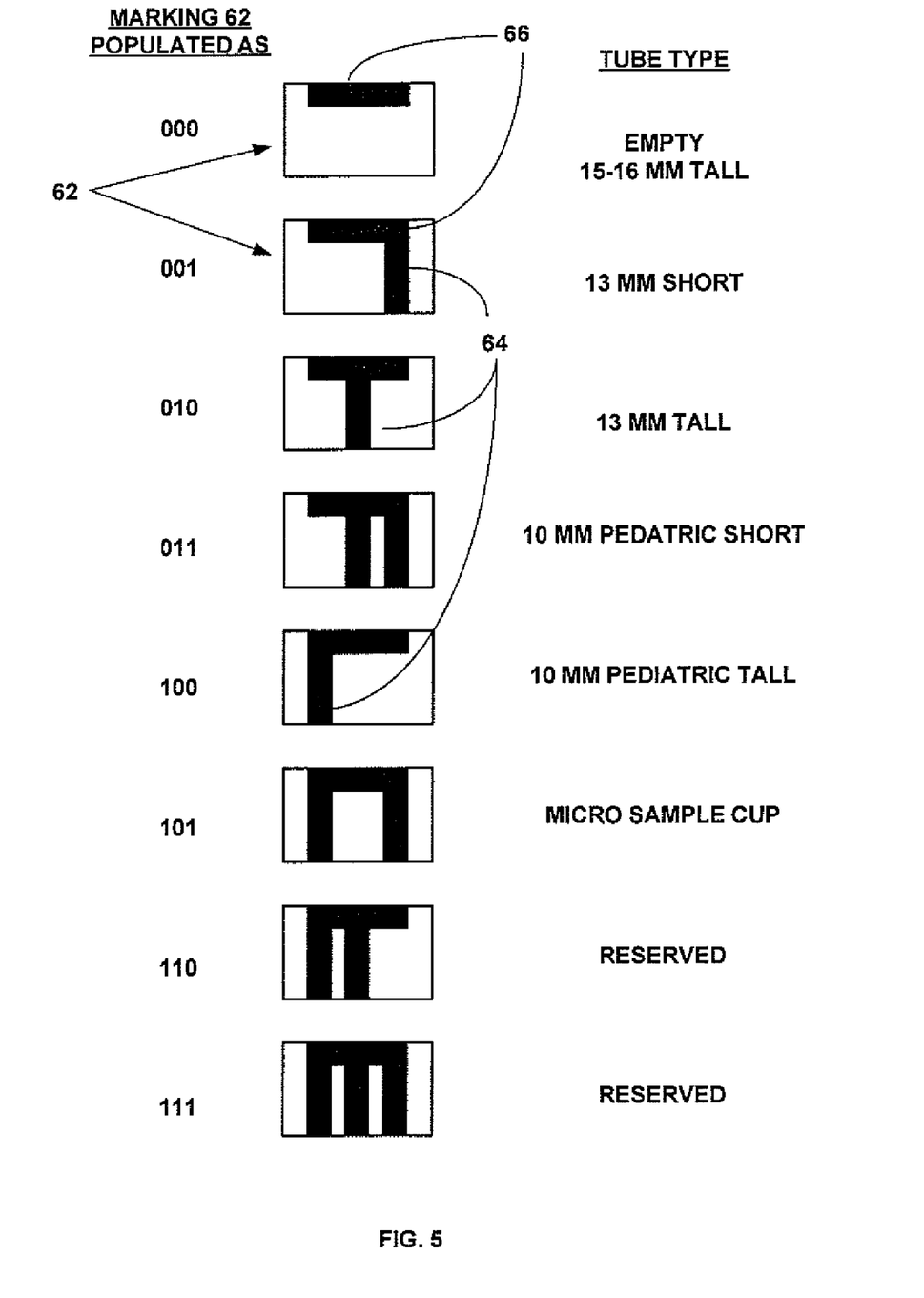
FIG. 5 is an illustration of insert markings identifiable by the vision system of FIG. 3; and, FIGS. 6-7 illustrate some of the different sample containers that can be identified by the vision system of FIG. 3.

An important feature of the vision system 50 of the present invention is a number of specially marked sample tube inserts 60 like illustrated in FIG. 5, each different insert 60 having a unique 3-D marking 62 affixed thereto, the inserts being of varying heights so as to position tubes 40 of various heights and diameters at a common aspiration level. In one embodiment, the 3-D markings 62 are populated with between 0 and 3 dark equi-spaced, vertical data bars 64 depending from a single horizontal guide bar 66. The presence and absence of vertical data bars 64 is determined by vision system 50 in order to identify the type and presence of inserts 60. In an exemplary embodiment, each vertical data bar is about 0.05 inches wide and has height extending to the bottom of marking 62, marking 62 being about 0.3 inches tall and about 0.9 inches wide. Using 3 data bars 64 allows for a maximum number of eight different inserts to be identifiable as shown in TABLE 1 below.

TABLE 1

| Insert Type | Data Bar Populated as 0 = Empty, 1 = Populated |
|---|---|
| Empty | 000 |
| 15-16 mm Diameter, Tall | |
| 13 mm Diameter, Short | 001 |
| 13 mm Diameter, Tall | 010 |
| 10 mm Diameter, Pediatric, Short | 011 |
| 10 mm Diameter, Pediatric, Tall | 100 |
| Micro Sample Cup | 101 |
| Reserved | 110 |
| Reserved | 111 |

FIG. 5 illustrates how 3-D markings 62 are populated with vertical data bars 64 depending from horizontal guide bar 66 and also shows the different tube types that correspond to the different 3-D markings 62. In practice, an operator simply places an insert 60 having the appropriate 3-D marking 62 affixed thereto into tube opening in rack 40 prior to placing a tube 40 therein. For example, if a patient sample is contained in a "short", 13 mm diameter primary tube 40 with length about 75 mm (as opposed to a "tall" tube with 100 mm length), then an insert 60 with marking 62 populated as 001 (second from top in FIG. 5) would be inserted into the tube opening in rack 40 prior to tube 40 being placed therein. The selection of patterns of vertical data bars 64 and the association with the indicated different types of tubs 40 is not unique nor limiting as to the marking 62 nor to the tube 40. Horizontal guide bar 66 is provided as an aid to properly locating and identifying marking 62 by the identification software program associated with vision system 50. Markings 62 are advantageously screen printed with flat black ink on a flexible retro-reflective sheeting having a permanent, pressure activated adhesive layer available as 3M™ ScotchLite™ Plus Reflective Graphic Film Series 680.

Figure 6:
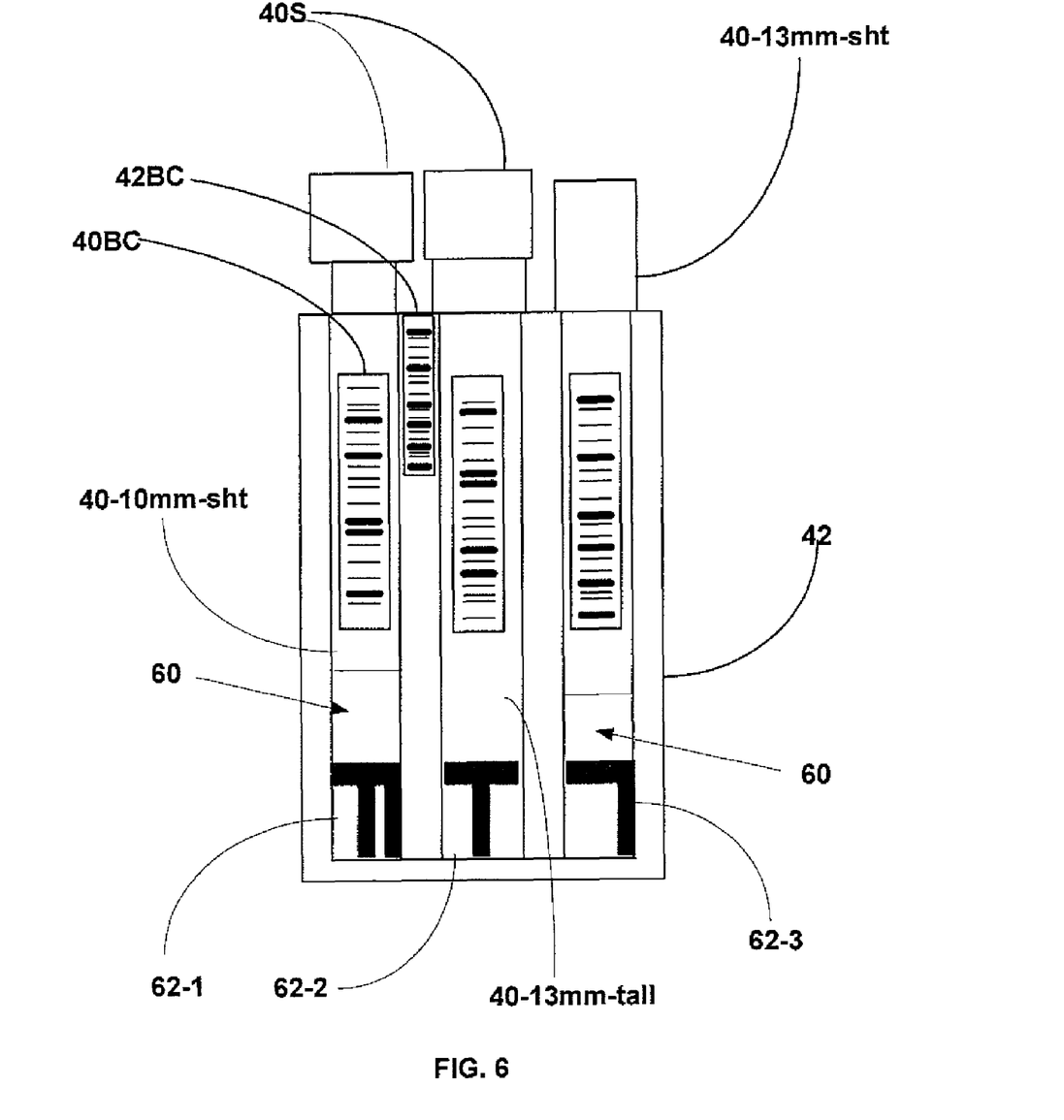
Figure 7:
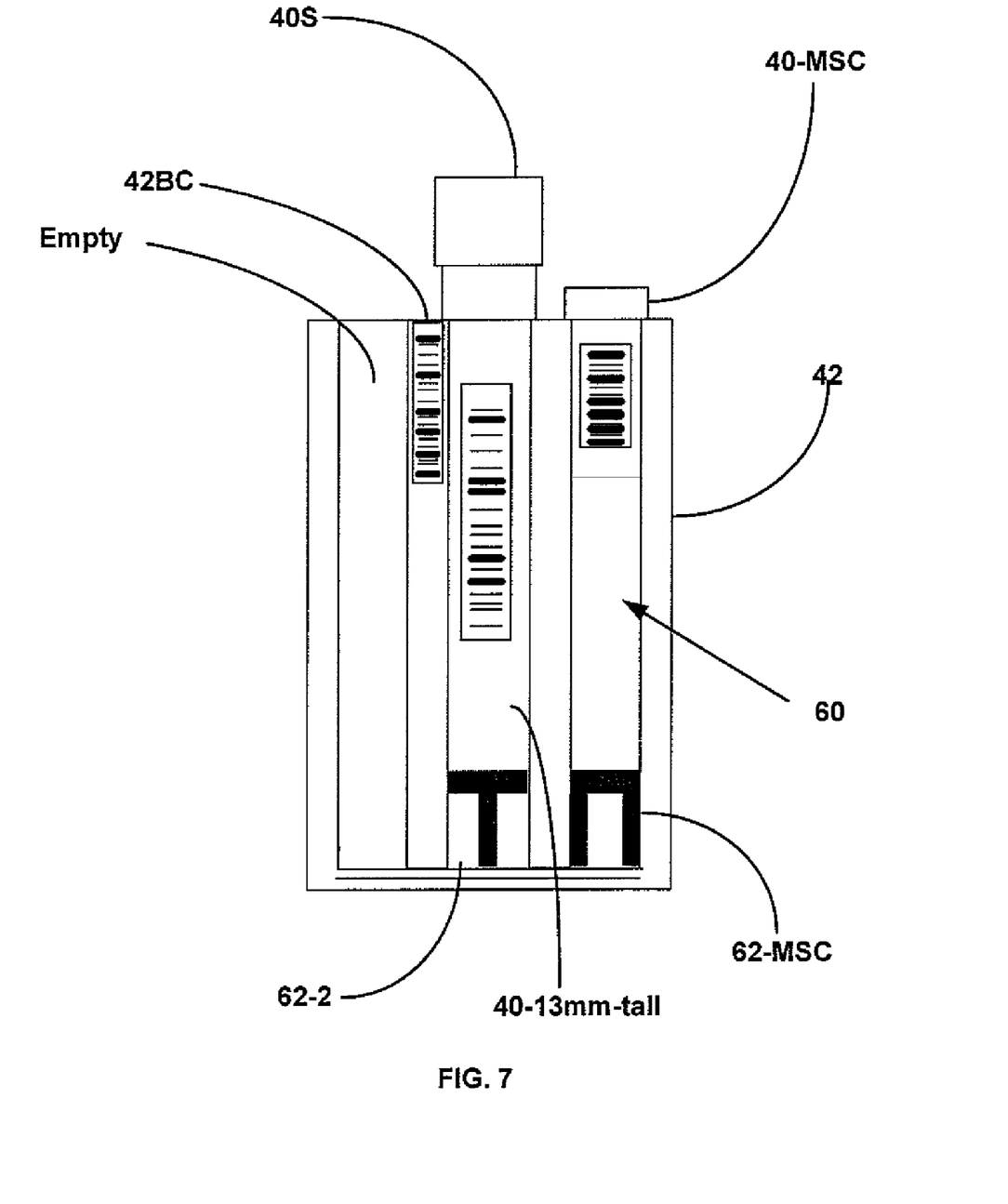

FIGS. 6 and 7 illustrate examples of various sample racks 40, tubes 40, markings 62, presence and/or absence of a stopper 40S on tubes 40. FIG. 6 in particular illustrates a tube bar code 40BC on a stoppered "short" pediatric tube 40-10 mm-sht with insert 60 having 3-D marking 62-1 populated as 011 as well as a non-stoppered "short" primary 13 mm tube 40-13 mm-sht having 3-D marking 62-3 populated as 001. In addition, rack 42 is seen as labeled with a rack identifying barcode 42BC. FIG. 7 illustrates an instance wherein the leftmost opening in rack 42 is empty and wherein the rightmost opening has an insert 60-4 placed beneath a Micro Sample Cup 40-MSC, insert 60-4 being marked with 3-D marking 62-MSC populated as 101 in accord with FIG. 5.

Figure 3:
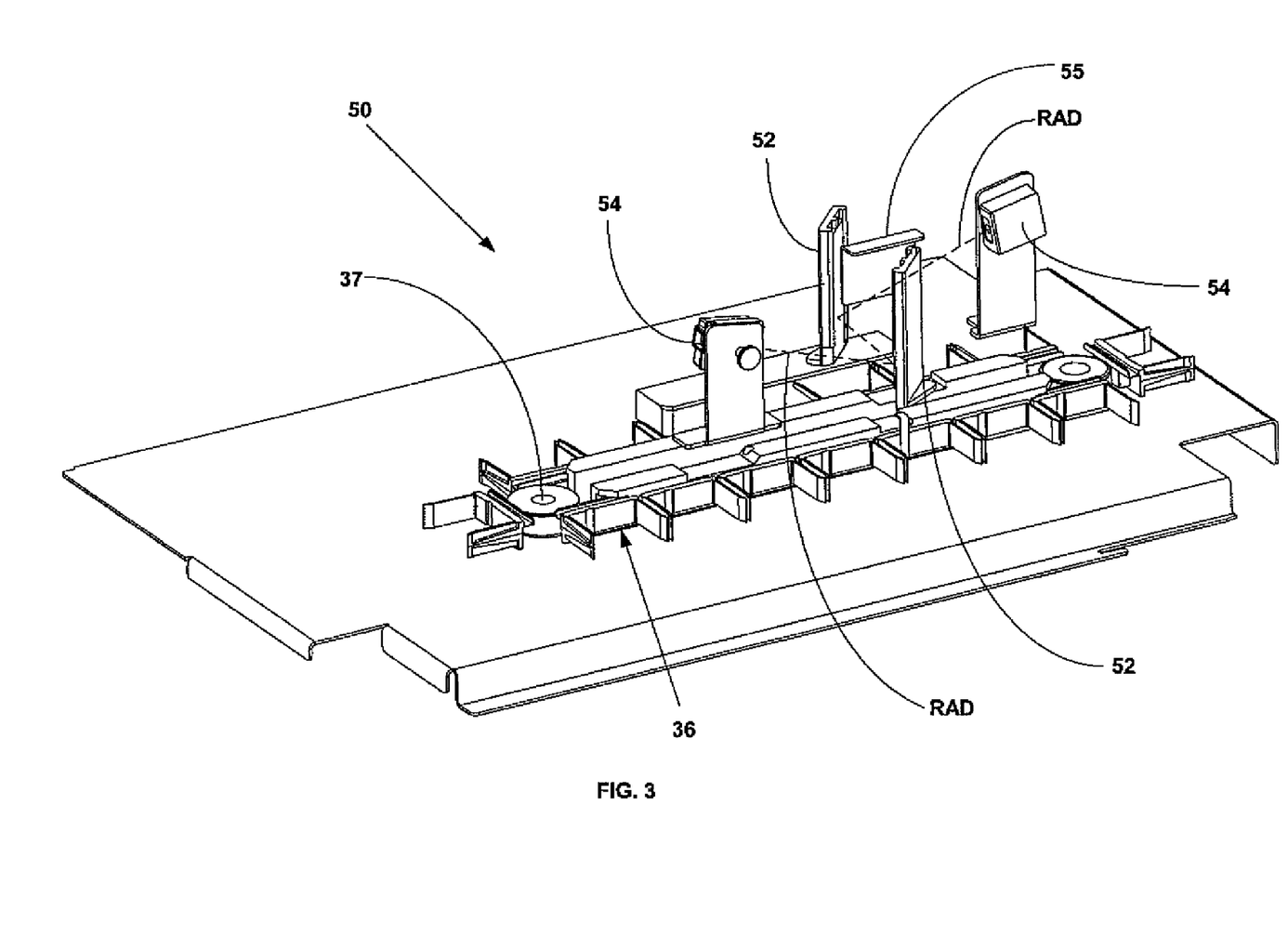
FIG. 3 is a perspective schematic illustration of the vision system exemplary of the present invention.
Figure 4:
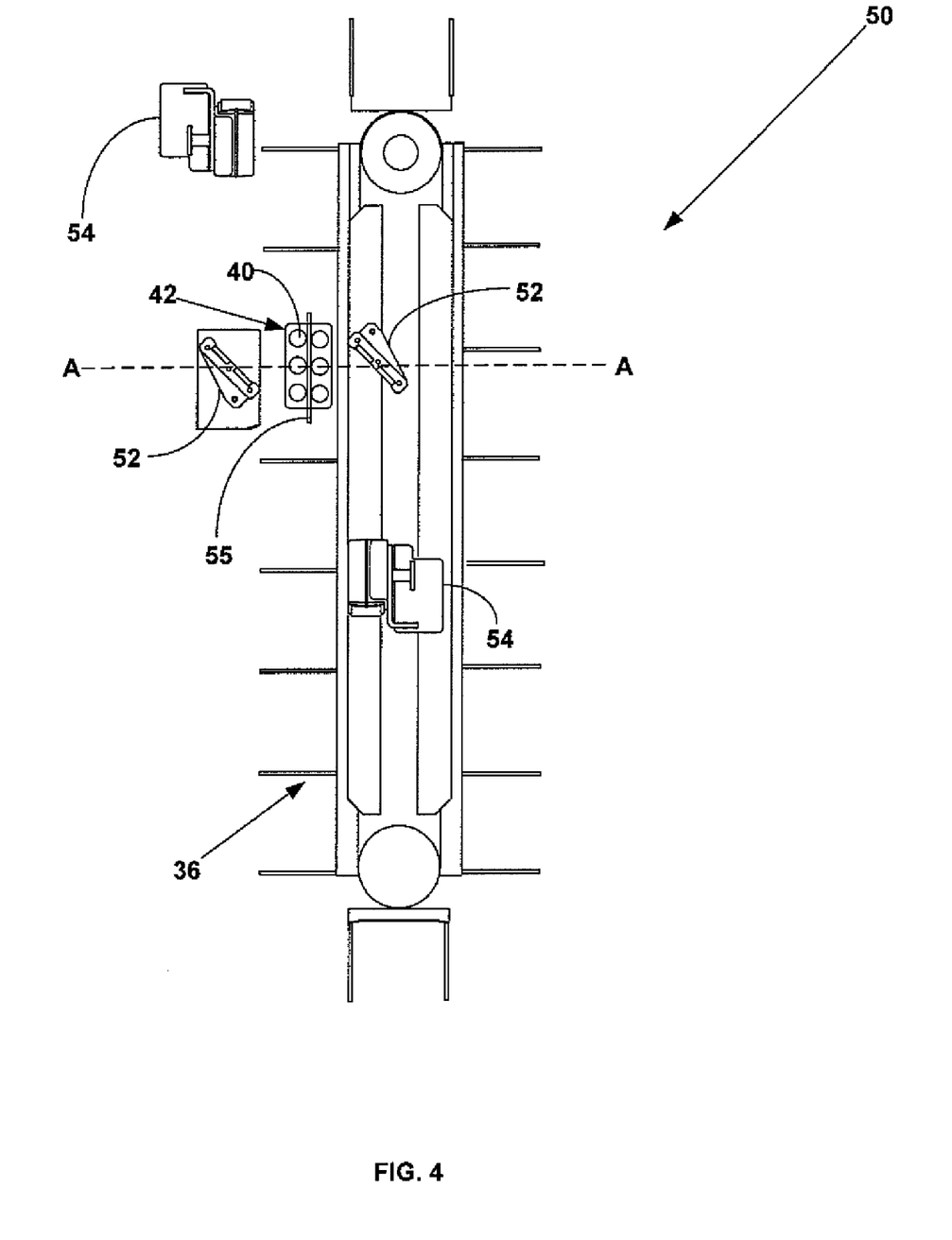
FIG. 4 is a top plan schematic view of the vision system of FIG. 3.

In an exemplary embodiment, sample rack 42 carries a maximum of 6 test tubes 40, 3 on each side of rack 42. The transport system 36 slides each rack 42 in a elongate circular pattern such that each test tube 40 of interest is centered between a pair of front surface mirrors 52 positioned at an angle so that a beam of interrogating radiation RAD emitted from the pair of imagers 54 typically employing a red LED for illumination is reflected from the exposed surface of tube 40 back to the imagers 54 for analysis. Using conventional software identification techniques, the imagers 54 capture a 2 dimensional VGA picture of marking 62 and process the image for identification of the test tube 40. After image processing is complete for this a first tube 40, transport system 36 moves rack 42 such that the next test tube 40 in rack 42 is centered between mirrors 52 and the imaging process is repeated.

The orientation of rack 42 with respect to imagers 54 placed on the side of rack 42 require mirrors 52 to provide the reflection upon which the test tube 40 can be seen.

Optimal operation of vision system 50 requires proper orientation and centering of imagers 54 with respect to the test tubes 42 of interest. For proper detection processing, test tube 42 is advantageously located in the center of the image that is taken by imagers 54. A calibration process is employed to ensure that mirror 52, rack 42 and imager 54 are properly aligned within vision system 50. The calibration process is similar to processes used in conventional image processing and determines the following:

1. The pixel location of the start of reflector 55;
2. The width of the retro-reflective region on reflector 55; and,
3. The offset dimension of the insert 60 with respect to reflector 55.

The pixel location of the retro-reflective edge of reflector 55 is used by vision system 50 for the Cap/No Cap processing. Once this value is determined, it is stored in flash memory inside vision system 50 for subsequent usage. The difference value, the pixel location of the retro-reflective start location, and the width of the retro-reflective region provide information to computer 15 that will allow for proper horizontal and vertical alignment of the mirror 52 and/or the imager 54. There will be a known width of the region that must be maintained and calibrated also. In addition there will be a known pixel location of the retro-reflective start line that must be adjusted. The host computer 15 will query the vision system 50 for the difference value. This value will enable the test tube rack 42 to be moved to the correct horizontal position. A remote computer 15 may also be employed in practicing the present invention.

From the above description, vision system 50 provides imaging and analytical capabilities so as to be able to identify and decode barcodes on sample tubes 40 and sample rack 42, markings 62 on inserts 60, the presence or absence of a sample tube 40 within rack 42, the presence or absence of a stopper 40S capping a sample tube 40, and the identification of a number of different types of sample containers including tubes and cups.

A number of other advantages also achieved using the vision system 50 of present invention, including:

1. In the instance of Small or Micro Sample Cups, 2-D imager 54 can optionally confirm that an evaporation reduction lid is in a closed position and to appropriately govern aspiration so as to aspirate the entire liquid sample. In addition, when an operator pours sample from a bar-coded sample tube into the Micro Sample Cup, a 2-D bar-code printer can be programmed to automatically print a 2-D bar-code to be placed upon the Sample Cup as a means of reliable identifying/tracking the sample tube.
2. In the event the 2-D imager 54 finds no readable marking in a rack tube opening or slot that contains a sample, an error may be posted warning the operator of the problem. This eliminates "lost samples" arising from poorly printed or positioned markings on tubes.

It should be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention.

Accordingly, while the present invention has been described herein in detail in relation to specific embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

We claim:

1. An automated vision system for use in a clinical analyzer, comprising:

a sample tube rack having at least one row of openings closed at a bottom portion thereof capable of containing different types of sample tubes;

sample tube inserts disposed in said bottom portion of at least one of said openings, the inserts having different tube type identification markings thereon to identify the type of sample tube in said at least one opening; and imaging devices disposed proximate said sample tube rack, the devices programmed to identify the markings on said inserts, wherein the sample tube inserts are of varying heights so as to position tubes of various heights at a common aspiration level.

2. The automated vision system of claim 1, wherein the imaging devices are disposed on opposing sides of said sample tube rack and are capable of simultaneously identifying the tube type identification markings on two of said types of sample tubes.

3. The automated vision system of claim 1, wherein the tube type identification markings identify whether a tube comprises a primary tube, a pediatric tube, a sample cup, or a micro sample.

4. The automated vision system of claim 1, wherein the tube type identification markings comprise a number of vertical bars.

5. The automated vision system of claim 4, wherein the tube type identification markings depend from a horizontal bar.

6. The automated vision system of claim 1, further comprising a computer comprising software written in a machine language and programmed to control said imaging devices and to provide image analysis of said tube type identification markings, wherein said computer is programmed to identify whether or not a tube is stoppered.

7. The automated vision system of claim 6, wherein said computer is programmed to display an error signal if the tube type identification markings cannot be read by the imaging devices.

8. A clinical analyzer having an automated vision system installed thereon, said analyzer adapted for analyzing patient samples carried in a sample tube rack having openings at a bottom portion thereof for containing different types of sample tubes, the sample tube rack also having sample tube inserts disposed in said bottom portion of at least one of said openings, the inserts having different tube type identification markings to uniquely identify a type of sample tube in said at least one opening, wherein said vision system comprises imaging devices disposed proximate said sample tube rack, the devices programmed to identify the markings on said inserts, and a computer comprising software written in a machine language and programmed to control said imaging devices and to provide image analysis of said tube type identification markings, and wherein the inserts are of varying heights so as to position tubes of various heights at a common aspiration level.

9. The analyzer of claim 8, wherein the tube type identification markings identify whether a tube comprises a primary tube, a pediatric tube, a sample cup, or a micro sample.

10. The analyzer of claim 8, wherein the tube type identification markings comprise a number of vertical bars.

11. The analyzer of claim 10, wherein the tube type identification markings depend from a horizontal bar.

12. The analyzer of claim 8, wherein the vision system is programmed to identify whether or not a tube is stoppered.

13. The analyzer of claim 8, wherein the vision system is programmed to display an error if the markings cannot be read by the imaging devices.

* * * * *